(12) United States Patent
Ishikawa et al.

(10) Patent No.: US 6,833,462 B2
(45) Date of Patent: Dec. 21, 2004

(54) PROCESS FOR PREPARING ACRYLATE COMPOUND

(75) Inventors: Shinichi Ishikawa, Shinnanyo (JP); Hisao Eguchi, Shinnanyo (JP)

(73) Assignee: Tosoh Corporation, Yamaguchi (JP)

( * ) Notice: Subject to any disclaimer, the term of this patent is extended or adjusted under 35 U.S.C. 154(b) by 6 days.

(21) Appl. No.: 10/303,905

(22) Filed: Nov. 26, 2002

(65) Prior Publication Data

US 2003/0139613 A1 Jul. 24, 2003

(30) Foreign Application Priority Data

Nov. 28, 2001 (JP) ........................................ 2001-363270
Mar. 8, 2002 (JP) ........................................ 2002-064039

(51) Int. Cl.⁷ .................... C07D 315/00; C07D 307/02; C07C 69/52
(52) U.S. Cl. ...................... 549/420; 549/427; 549/475; 549/499; 549/501; 560/205; 560/220
(58) Field of Search ................................. 549/420, 427, 549/475, 499, 501; 560/205, 220

(56) References Cited

U.S. PATENT DOCUMENTS 4,293,499 A * 10/1981 Hughes .................... 260/410.9

FOREIGN PATENT DOCUMENTS

| JP | 48-39425 | * | 6/1973 |
| JP | 11-222460 | * | 8/1999 |
| WO | WO 81/00846 | * | 4/1981 |

OTHER PUBLICATIONS

Ndong Mebah et al, "A convenient use of polyphosphoric acid in the esterification reaction between (meth)acrylic acid and (cyclo)alkenes" New Journal of Chemistry, vol. 17(12), pp. 835–841. (1993).*
Pavlov et al, Bulletin de la Societe Chimique de France, No. 12, pp. 2985–2986 (1974).*

\* cited by examiner

*Primary Examiner*—Richard L. Raymond
*Assistant Examiner*—Zachary C. Tucker
(74) *Attorney, Agent, or Firm*—Sughrue Mion, PLLC

(57) ABSTRACT

An acrylate compound of formula (4):

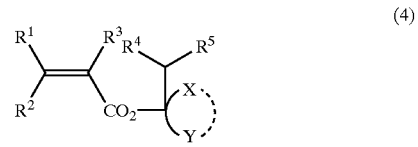

(4)

is produced by allowing an acrylic acid compound of formula (1):

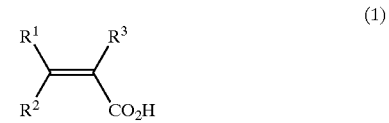

(1)

to react with an unsaturated compound of formula (2) or (3):

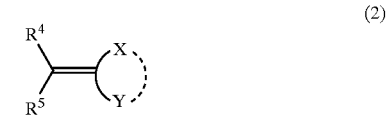

(2)

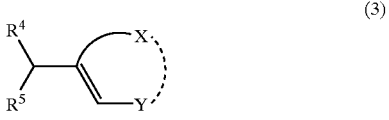

(3)

In formulae (1) through (4), $R^1$ and $R^2$ are H or F, $R^3$ is H, F, or an alkyl, alkenyl, fluoroalkyl or fluoroalkenyl group, $R^4$ and $R^5$ are H, halogen, or an alkyl, alkenyl, halogenated alkyl or halogenated alkenyl group; and X and Y are an unsubstituted or substituted hydrocarbon group, and dashed line - - - means that X and Y may be bonded together to form a cyclic structure.

20 Claims, No Drawings

PROCESS FOR PREPARING ACRYLATE COMPOUND

BACKGROUND OF THE INVENTION (1) Field of the Invention

This invention relates to a process for preparing an acrylate compound which is expected to be used as a raw material for functional polymers, pharmaceuticals and pesticides.

(2) Description of the Related Art

In recent years acrylate compounds have provided a great attraction, for example, as monomers used for producing a resist for advanced semiconductor lithography. Especially acrylate compounds having a tertiary ester skeletal structure capable of being dissociated with an acid are suitable therefor in view of lithography mechanism.

As specific examples of the acrylate or methacrylate compounds having such a skeletal structure capable of being dissociated with an acid, there can be mentioned acrylates and methacrylates having an acid-dissociatable group such as a 2-methyl-2-adamantyl group or a 8-ethyl-8-tricyclodecanyl group (Japanese Unexamined Patent Publication [hereinafter abbreviated to "JP-A"] No. 2001-188352, JP-A H11-305444 and JP-A H9-43848), and α-trifluoromethylacrylates having an acid-dissociatable group such as a 2-methyl-2-adamantyl group or a 1-alkyl-1-cycloalkyl group (JP-A 2001-302728).

The above-mentioned acrylate compounds are prepared, for example, by the following known processes.

A first type process comprises allowing an acrylic acid chloride compound to react with an alcohol or a metal alcoholate in the presence of a base. The first type process includes, for example, a process wherein 2-methyl-2-adamantanol is allowed to react with acryloyl chloride or methacryloyl chloride in the presence of triethylamine to give a corresponding acrylate or methacrylate compound (for example, JP-A H11-305444, JP-A 2000-122294, JP-A 2000-229911 and JP-A 2001-188352), and a process wherein 8-ethyl-8-cyclododecanol is allowed to react with methacryloyl chloride in the presence of triethylamine (JP-A 2001-188352). The first type process further includes a process wherein 2-adamantanone is allowed to react with methyllithium or a methyl Grignard reagent to give a Li or Mg salt of 2-methyl-2-adamantanonol, and then, methacryloyl chloride is added in a solution of the thus-obtained Li or Mg salt to give a corresponding methacrylate compound (JP-A H10-182552 and JP-A 2000-229911).

The first type process has a problem such that acryloyl chloride and methacryloyl chloride are not readily available and are expensive, and are difficult to handle because these acid chlorides easily produce a large amount of hydrogen chloride gas when they are contacted with moisture in the air.

As a process wherein acryloyl chloride and methacryloyl chloride are not used to overcome the first type process, a second process has been proposed which includes, for example, a process wherein acrylic acid is allowed to react with a tertiary alcohol such as 1-ethyl-1-cyclohexanol (JP-A 2000-319226).

However, in the second process, large amounts of a carboxylic acid anhydride such as acetic anhydride and an amine compound such as triethylamine must be used to smoothly carry out the reaction, with the result of reduction in efficiency and cost for production.

SUMMARY OF THE INVENTION

In view of the foregoing, a primary object of the present invention is to provide a process for preparing acrylate compounds whereby the object compounds can be prepared with high efficiency without the above-mentioned problems of the prior art, namely, with a reduced cost and an enhanced safety.

Thus, in accordance with the present invention, there is provided a process for preparing an acrylate compound represented by the following formula (4):

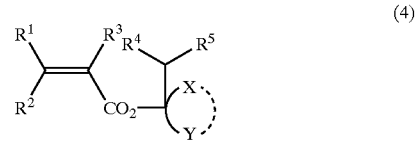

wherein $R^1$ and $R^2$ independently represent a hydrogen atom or a fluorine atom, $R^3$ represents a hydrogen atom, a fluorine atom, an alkyl group, an alkenyl group, a fluoroalkyl group, or a fluoroalkenyl group, $R^4$ and $R^5$ independently represent a hydrogen atom, a halogen atom, an alkyl group, an alkenyl group, a halogenated alkyl group, or a halogenated alkenyl group; and X and Y independently represent a hydrocarbon group, which may have at least one substituent selected from the group consisting of a halogen-containing substituent, an oxygen-containing substituent and a nitrogen-containing substituent, and dashed line - - - - - means that X and Y may be bonded together to form a cyclic structure;

which comprises allowing an acrylic acid compound represented by the following formula (1):

wherein $R^1$, $R^2$ and $R^3$ are the same as defined above for formula (4), to react with an unsaturated compound represented by the following formula (2) or (3):

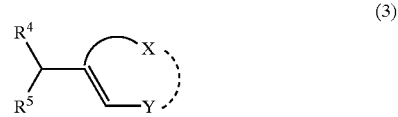

wherein $R^4$, $R^5$, X and Y are the same as defined above for formula (4).

DESCRIPTION OF THE PREFERRED EMBODIMENT

The acrylic acid compound used as a raw material in the process of the present invention is represented by the above formula (1). In formula (1), $R^1$ and $R^2$ independently represent a hydrogen atom or a fluorine atom, and preferably represent a hydrogen atom.

In formula (1), $R^3$ represents a hydrogen atom, a fluorine atom, an alkyl group, an alkenyl group, a fluoroalkyl group or a fluoroalkenyl group. $R^3$ is preferably selected from a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, and a $C_2$–$C_4$ straight-chain or branched fluoroalkenyl group. As specific examples of the alkyl group, there can be mentioned methyl, ethyl, propyl and butyl groups. As specific examples of the alkenyl group, there can be mentioned ethenyl, 1-propenyl, allyl and 1-, 2- or 3-butenyl groups. As specific examples of the fluoroalkyl group, there can be mentioned fluoromethyl, fluoroethyl, fluoropropyl and fluorobutyl groups. As specific examples of the fluoroalkenyl group, there can be mentioned fluoroethenyl, fluoro-1-propenyl, fluoroallyl and fluoro-1-butenyl, fluoro-2-butenyl and fluoro-3-butenyl groups.

Preferable examples of the acrylic acid compound of formula (1) are those wherein $R^1$ and $R^2$ are a hydrogen atom, and $R^3$ is selected from a hydrogen atom, a fluorine atom, an alkyl group (preferably a $C_1$–$C_4$ straight-chain or branched alkyl group), an alkenyl group (preferably a $C_2$–$C_4$ straight-chain or branched alkenyl group), a fluoroalkyl group (preferably a $C_1$–$C_4$ straight-chain or branched fluoroalkyl group) and a fluoroalkenyl group (preferably a $C_2$–$C_4$ straight-chain or branched fluoroalkenyl group).

As specific examples of the acrylic acid compound, there can be mentioned acrylic acid, methacrylic acid, α-ethylacrylic acid, α-n-propylacrylic acid, α-isopropylacrylic acid, α-n-butylacrylic acid, α-isobutylacrylic acid, α-s-butylacrylic acid, α-allylacrylic acid, α-t-butylacrylic acid, α-fluoromethylacrylic acid, α-trifluoromethylacrylic acid, α-fluoroacrylic acid, α-difluoroacrylic acid, α-trifluoroacrylic acid, α-fluoroethylacrylic acid, α-difluoroethylacrylic acid, α-trifluoroethylacrylic acid, α-tetrafluoroethylacrylic acid, α-perfluoroethylacrylic acid, α-fluoropropylacrylic acid, α-difluoropropylacrylic acid, α-trifluoropropylacrylic acid, α-tetrafluoropropylacrylic acid, α-pentafluoropropylacrylic acid, α-hexafluoropropylacrylic acid, α-perfluoropropylacrylic acid, α-fluorobutylacrylic acid, α-difluorobutylacrylic acid, α-trifluorobutylacrylic acid, α-tetrafluorobutylacrylic acid, α-pentafluorobutylacrylic acid, α-hexafluorobutylacrylic acid, α-heptafluorobutylacrylic acid, α-octafluorobutylacrylic acid, α-perfluorobutylacrylic acid, α-fluoroallylacrylic acid, α-difluoroallylacrylic acid, α-trifluoroallylacrylic acid, α-tetrafluoroallylacrylic acid, α-perfluoroallylacrylic acid, α-trifluoromethyl-β-fluoroacrylic acid, α-trifluoromethyl-β,β-difluoroacrylic acid and α,β,β-trifluoroacrylic acid.

Of these, α-trifluoromethylacrylic acid, α-trifluoroethylacrylic acid, α-perfluoroethylacrylic acid, α-perfluoropropylacrylic acid, α-perfluorobutylacrylic acid, α-fluoroacrylic acid, acrylic acid and methacrylic acid are preferable. α-trifluoromethylacrylic acid, acrylic acid and methacrylic acid are especially preferable.

The unsaturated compound used as a raw material in the process of the present invention is represented by the formula (2) or (3), which has at least one carbon-carbon double bond in the structure and at least one carbon atom of the carbon-carbon double bond is bonded to only carbon atoms, namely, is not directly bonded to any atom other than carbon atom. The skeleton of the unsaturated compound may be either a chain-like structure including a straight chain structure and a branched structure, or an alicyclic structure.

The above-mentioned unsaturated compound of formula (2) or (4) includes, for example, those which are represented by the following formulae (7) through (13).

Compounds represented by the following formula (7):

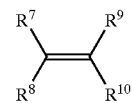

(7)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^9$ and $R^{10}$ independently represent a $C_1$–$C_{10}$ straight-chain or branched alkyl group, or a $C_2$–$C_{10}$ straight-chain or branched alkenyl group;

compounds represented by the following formula (8):

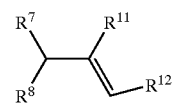

(8)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{11}$ and $R^{12}$ independently represent a $C_1$–$C_{10}$ straight-chain or branched alkyl group, or a $C_2$–$C_{10}$ straight-chain or branched alkenyl group;

compounds represented by the following formula (9):

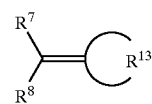

(9)

wherein $R^7$ and $R^8$ independently represent a hydrogen atom, a halogen atom, a $C_1$–$C_4$ straight chain or branched alkyl group, a $C_2$–$C_4$ straight chain or branched alkenyl group, a $C_1$–$C_4$ straight-chain or branched haloalkyl group, or a $C_2$–$C_4$ straight-chain or branched haloalkenyl group, and $R^{13}$ represents a $C_2$–$C_{15}$ straight chain or branched alkylene group or a $C_2$–$C_{15}$ straight-chain or branched alkenylene group;

compounds represented by the following formula (10):

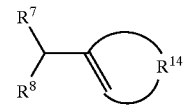

(10)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{14}$ represents a $C_1$–$C_{15}$ alkylene group, or a $C_2$–$C_{15}$ alkenylene group;

compounds represented by the following formula (11):

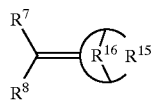

(11)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, $R^{15}$ represents a $C_1$–$C_{15}$ alkylene group or a $C_2$–$C_{15}$ alkenylene group, and $R^{16}$ represents a $C_1$–$C_3$ alkylene group;

compounds represented by the following formula (12):

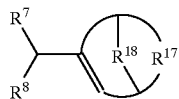

(12)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, $R^{17}$ represents a $C_1$–$C_{15}$ alkylene group or a $C_2$–$C_{15}$ alkenylene group, and $R^{18}$ represents a $C_1$–$C_3$ alkylene group; and compounds represented by the following formula (13):

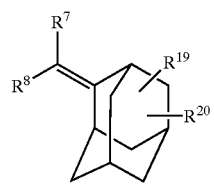

(13)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{19}$ and $R^{20}$ independently represent a hydrogen atom, a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom.

As examples of the unsaturated compound of the above formula (9), there can be mentioned those which are represented by the following formulae (14) through (20).

Compounds represented by the following formula (14):

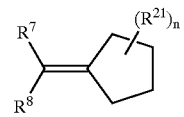

(14)

wherein $R^7$ and $R^8$ independently represent a hydrogen atom, a halogen atom, a $C_1$–$C_4$ straight-chain or branched alkyl group, a $C_2$–$C_4$ straight-chain or, branched alkenyl group, a $C_1$–$C_4$ straight-chain or branched haloalkyl group, or a $C_2$–$C_4$ straight-chain or branched haloalkenyl group, and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 8;

compounds represented by the following formula (15):

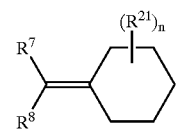

(15)

wherein $R^7$, $R^8$ and $R^{21}$ are the same as defined above for formula (14), and n is an integer in the range of 0 to 10;

compounds represented by the following formula (16):

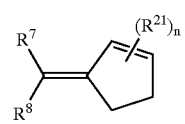

(16)

wherein $R^7$, $R^8$ and $R^{21}$ are the same as defined above for formula (14), and n is an integer in the range of 0 to 6;

compounds represented by the following formula (17):

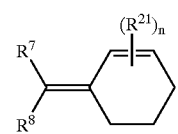

(17)

wherein $R^7$, $R^8$ and $R^{21}$ are the same as defined above for formula (14), and n is an integer in the range of 0 to 8;

compounds represented by the following formula (18):

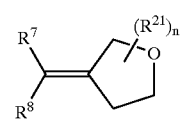

(18)

wherein $R^7$, $R^8$ and $R^{21}$ are the same as defined above for formula (14), and n is an integer in the range of 0 to 6;

compounds represented by the following formula (19):

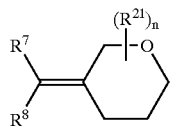

(19)

wherein $R^7$, $R^8$ and $R^{21}$ are the same as defined above for formula (14), and n is an integer in the range of 0 to 8; and compounds represented by the following formula (20):

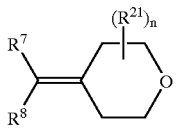

(20)

wherein $R^7$, $R^8$ and $R^{21}$ are the same as defined above for formula (14), and n is an integer in the range of 0 to 8.

As examples of the unsaturated compound of the above formula (10), there can be mentioned those which are represented by the following formulae (21) through (27).

Compounds represented by the following formula (21):

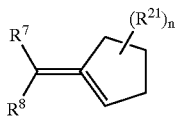

(21)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 7;

compounds represented by the following formula (22):

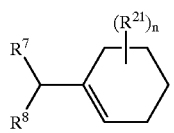

(22)

wherein $R^7$, $R^8$ and $R^{21}$ are the same as defined above for formula (21), and n is an integer in the range of 0 to 9;

compounds represented by the following formula (23):

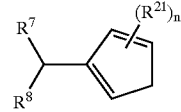

(23)

wherein $R^7$, $R^8$ and $R^{21}$ are the same as defined above for formula (21), and n is an integer in the range of 0 to 5;

compounds represented by the following formula (24):

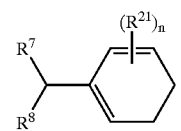

(24)

wherein $R^7$, $R^8$ and $R^{21}$ are the same as defined above for formula (21), and n is an integer in the range of 0 to 7;

compounds represented by the following formula (25):

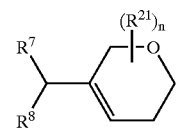

(25)

wherein $R^7$, $R^8$ and $R^{21}$ are the same as defined above for formula (21), and n is an integer in the range of 0 to 5;

compounds represented by the following formula (26):

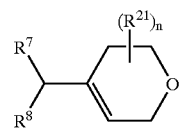

(26)

wherein $R^7$, $R^8$ and $R^{21}$ are the same as defined above for formula (21), and n is an integer in the range of 0 to 7; and compounds represented by the following formula (27):

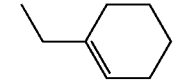

(27)

wherein $R^7$, $R^8$ and $R^{21}$ are the same as defined above for formula (21), and n is an integer in the range of 0 to 7.

Among the unsaturated compounds of formula (22), 1-ethylcyclohexene represented by the following formula (36) is especially preferable.

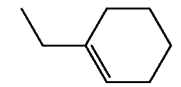

(36)

As examples of the unsaturated compound of the above formula (11), there can be mentioned those which are represented by the following formulae (28) through (31).

Compounds represented by the following formula (28):

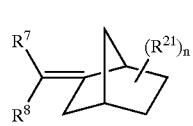
(28)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 8;

compounds represented by the following formula (29):

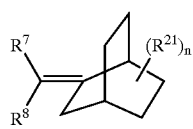
(29)

wherein $R^7$, $R^8$ and $R^{21}$ are the same as defined above for formula (28), and n is an integer in the range of 0 to 8;

compounds represented by the following formula (30):

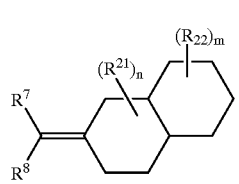
(30)

wherein $R^7$, $R^8$ and $R^{21}$ are the same as defined above for formula (28), n is an integer in the range of 0 to 5, $R^{22}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_2$–$C_4$ alkoxy group, an amino group, a carboxyl group, an ester group, a carbonyl group or a halogen atom, and m is an integer in the range of 0 to 8; and, compounds represented by the following formula (31):

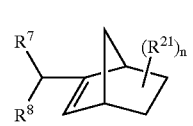
(31)

wherein $R^7$, $R^8$, $R^{21}$ and $R^{22}$ are the same as defined above for formulae (28) and (30), and n is an integer in the range of 0 to 5, and m is an integer in the range of 0 to 8.

As examples of the unsaturated compound of the above formula (12), there can be mentioned those which are represented by the following formulae (32) through (35).

Compounds represented by the following formula (32):

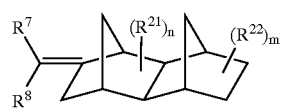
(32)

wherein $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 8;

compounds represented by the following formula (33):

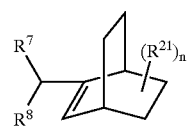
(33)

wherein $R^7$, $R^8$ and $R^{21}$ are the same as defined above for formula (32), and n is an integer in the range of 0 to 8;

compounds represented by the following formula (34):

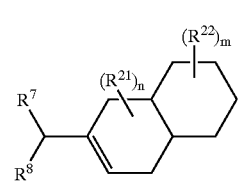
(34)

wherein $R^7$, $R^8$ and $R^{21}$ are the same as defined above for formula (32), n is an integer in the range of 0 to 5, $R^{22}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and m is an integer in the range of 0 to 8; and, compounds represented by the following formula (35):

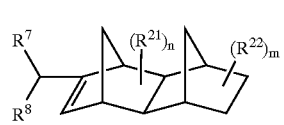
(35)

wherein $R^7$, $R^8$, $R^{21}$ and $R^{22}$ are the same as defined above for formulae (32) and (34), and n is an integer in the range of 0 to 8, and m is an integer in the range of 0 to 8.

Among the unsaturated compounds of formula (13), 2-methyleneadamantane represented by the following formula (37) is especially preferable.

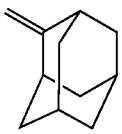

(37)

In $R^7$, $R^8$ and $R^{19}$ to $R^{22}$ of the above formulae (7) to (35), the terms "$C_1$–$C_4$ straight-chain or branched haloalkyl group" and "$C_2$–$C_4$ straight-chain or branched haloalkenyl group" mean a $C_1$–$C_4$ straight-chain or branched alkyl group and a $C_2$–$C_4$ straight-chain or branched alkenyl group, each having one or more halogen substituents, respectively. The halogen substituent includes chlorine, bromine, iodine and fluorine. The term "halogen atom" in $R^7$, $R^8$ and $R^{19}$ to $R^{22}$ of the formulae (7) to (35) means chlorine, bromine, iodine and fluorine atoms.

The unsaturated compounds of formulae (2) and (3) used in the process of the present invention can be easily prepared, for example, by a method wherein a commercially available corresponding tertiary alcohol is subjected to intramolecular dehydration reaction, or a method wherein a commercially available corresponding carbonyl compound is subjected to Wittig reaction.

The amount of the unsaturated compound of formula (2) or (3) used in the process of the present invention is not particularly limited, but is preferably in the range of 1 mol to 20 mols per mol of the acrylic acid compound (1). When the amount of the unsaturated compound is too small, the conversion of the acrylic acid compound tends to be poor. In contrast, when the amount of the unsaturated compound is too large, the production cost is liable to be increased because many unsaturated compounds including 2-methyleneadamantane are expensive.

When the acrylic acid compound of formula (1) is allowed to react with the unsaturated compound of formula (2) or (3) by the process of the present invention, the acrylate compound of formula (4) can be produced with an enhanced efficiency. Especially when an acrylic acid compound represented by the following formula (38):

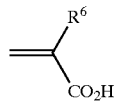

(38)

wherein $R^6$ is a hydrogen atom, a fluorine atom, an alkyl group (preferably a $C_1$–$C_4$ straight-chain or branched alkyl group), an alkenyl group (preferably a $C_2$–$C_4$ straight-chain or branched alkenyl group), a fluoroalkyl group (preferably a $C_1$–$C_4$ straight-chain or branched fluoroalkyl group), or a fluoroalkenyl group (preferably a $C_2$–$C_4$ straight-chain or branched fluoroalkenyl group), is allowed to react with 2-methyleneadamantane represented by the following formula (37):

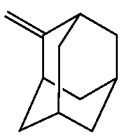

(37)

a methyladamantyl acrylate compound represented by the following formula (40) can be produced with greatly enhanced efficiency.

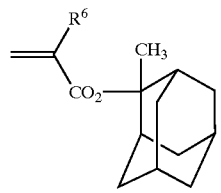

(40)

wherein $R^6$ is the same as defined above for formula (38).

This makes a striking contrast with the conventional process wherein a methyladamantyl acrylate compound having a fluoroalkyl group such as 2-methyl-2-adamantyl α-trifluoromethylacrylate (MAFAC) is produced in a low yield.

The reaction of the acrylic acid compound of formula (1) with the unsaturated compound of formula (2) or (3) can be carried out in the presence of a catalyst to more enhance the efficiency. The catalyst is preferably an acidic catalyst, which includes, for example, hydrogen fluoride, hydrogen chloride, hydrogen bromide, hydrogen iodide, nitric acid, phosphoric acid, sulfonic acid compounds, carboxylic acid compounds and Lewis acid compounds.

By the term "sulfonic acid compounds" used herein, we mean catalysts having a sulfonic acid group in the molecule structure. The sulfonic acid compounds are not particularly limited provided that they have a sulfonic acid group, and, as specific examples thereof, there can be mentioned inorganic sulfonic acids such as sulfuric acid, fluorosulfonic acid and chlorosulfonic acid; aliphatic sulfonic acids such as methanesulfonic acid, ethanesulfonic acid, propanesulfonic acid, allylsulfonic acid, butanesulfonic acid, pentanesulfonic acid, hexanesulfonic acid, heptanesulfonic acid, octanesulfonic acid, nonanesulfonic acid, decanesulfonic acid, dodecanesulfonic acid, tetradecanesulfonic acid and DL-camphor-10-sulfonic acid; substituted aliphatic sulfonic acids such as trifluoromethanesulfonic acid, aminomethanesulfonic acid, 2-bromoethanesulfonic acid, 2-(N-morpholino)ethanesulfonic acid, N,N'-bis(2-hydroxyethyl)-2-aminoethanesulfonic acid, N-(acetamido)-2-aminoethanesulfonic acid, N-2-hydroxyethylpiperazine-N'-2-ethanesulfonic acid, N-cyclohexyl-2-aminoethanesulfonic acid, 3-aminopropanesulfonic acid, N-cyclohexyl-2-hydroxy-3-aminopropanesulfonic acid, 3-chloro-2-hydroxypropanesulfonic acid, 3-(N-morpholino)propanesulfonic acid, 2-hydroxy-3-morpholinopropanesulfonic acid, 2-acrylamide-2-methylpropanesulfonic acid, 2-amino-5-methylbenzene-1-sulfonic acid, methallylsulfonic acid and taurine; aromatic sulfonic acids such as benzenesulfonic acid, p-chlorobenzenesulfonic acid, p-phenolsulfonic acid, guaiacol-4-sulfonic acid, p-styrenesulfonic acid, phenylhydrazine-p-sulfonic acid, 1,2-benzenedisulfonic acid, 1,3-benzenedisulfonic acid, 1,4-benzenedisulfonic acid, m-toluenesulfonic acid, p-toluenesulfonic acid, 2,4-dimethylbenzenesulfonic acid, 2,5-dimethylbenzenesulfonic acid, 2-mesitylenesulfonic acid, p-ethylbenzenesulfonic acid, 3,5-dichloro-2-hydroxybenzenesulfonic acid, 2,4,6-trinitrobenzenesulfonic acid, o-aminobenzenesulfonic acid, m-xylidine-6-sulfonic acid, 4-amino-2-methylbenzene-1-sulfonic acid, 4-amino-5-methoxy-2-methylbenzenesulfonic acid, 4-amino-2-chlorotoluene-5-sulfonic acid, 1-naphthalenesulfonic acid, 2-naphthalenesulfonic acid, 2,6- naphthalenedisulfonic acid, 2,7-naphthalenedisulfonic acid, 1-naphthol-2-sulfonic acid, 1-naphthol-4-sulfonic acid, 1-naphthol-8-sulfonic acid, 2-naphthol-6-sulfonic acid, 2-naphthol-3,6-disulfonic acid, 1-naphthylamine-4-sulfonic acid, 1-naphthylamine-6-sulfonic acid, 1-naphthylamine-8-sulfonic acid, 2-naphthylamine-1-sulfonic acid, 2-naphthylamine-6-sulfonic acid, 2,3-dihydroxynaphthalene-6-sulfonic acid, 2-amino-5-naphthol-7-sulfonic acid, 8-amino-1-naphthol-3,6-disulfonic acid, 8-aminonaphthalene-1,3,6-trisulfonic acid, 8-anilino-1-naphthalenesulfonic acid, 4,4'-diaminostilbene-2,2'-disulfonic acid, 7-iodo-8-hydroxyquinoline-5-sulfonic acid, diphenylamine-4-sulfonic acid, 1-pyrenesulfonic acid and sulfanilic acid; and sulfonic acid type cation-exchange resins such as Nafion (available from Du Pont Co.), sulfonic acid type Amberlist (available from Rohm & Haas Co.), sulfonic acid type Amberlite (available from Rohm & Haas Co.), sulfonic acid type Diaion (available from Mitsubishi Chem. Corp.), sulfonic acid type Duolite (available from Sumitomo Chem. Co.), sulfonic acid type Dowex (available from Dow Chem. Co.), sulfonic acid type Purolite (available from Purolite Co.) and sulfonic acid type Lewatit (available from Bayer AG).

By the term "carboxylic acid compounds" used herein, we mean catalysts having a carboxylic acid group in the molecule structure. The carboxylic acid compounds are not particularly limited provided that they have a carboxylic acid group, and, as specific examples thereof, there can be mentioned aliphatic carboxylic acids such as formic acid, acetic acid, propionic acid, butyric acid, valeric acid, caproic acid, heptanoic acid, caprylic acid, pelargonic acid, capric acid, n-undecylenic acid, acrylic acid, crotonic acid, isocrotonic acid, vinylacetic acid, methacrylic acid, angelic acid, tiglic acid, 2-pentenoic acid, 3-pentenoic acid, 4-pentenoic acid, α-ethylacrylic acid, β,β-dimethylacrylic acid, 2-hexenoic acid, 3-hexenoic acid, 4-hexenoic acid, 5-hexenoic acid, 2-methyl-2-pentenoic acid, 3-methyl-2-pentenoic acid, 4-methyl-2-pentenoic acid, 4-methyl-3-pentenoic acid, 2-heptenoic acid, 2-octenoic acid, 4-decenoic acid, 9-decenoic acid, 9-undecenoic acid, 10-undecenoic acid, 4-dodecenoic acid, 5-dodecenoic acid, propiolic acid, tetrolic acid, ethylpropiolic acid, n-propylpropiolic acid, isopropylpropiolic acid, n-butylpropiolic acid, t-butylpropiolic acid, n-amylpropiolic acid, 9-undecynoic acid, 2,4-pentadienoic acid, 2,4-hexadienoic acid, fluoroacetic acid, difluoroacetic acid, trifluoroacetic acid, chloroacetic acid, dichloroacetic acid, trichloroacetic acid, bromoacetic acid, dibromoacetic acid, tribromoacetic acid, iodoacetic acid, diiodoacetic acid, triiodoacetic acid, α-chloropropionic acid, β-chloropropionic acid, α-bromopropionic acid, β-bromopropionic acid, α-iodopropionic acid, β-iodopropionic acid, α-chloroacrylic acid, β-chloroacrylic acid, trichloroacrylic acid, α-bromoacrylic acid, β-bromoacrylic acid, α-iodoacrylic acid, β-iodoacrylic acid, α-chlorocrotonic acid, β-chlorocrotonic acid, γ-chlorocrotonic acid, α-bromocrotonic acid, β-bromocrotonic acid, γ-bromocrotonic acid, oxalic acid, malonic acid, succinic acid, glutaric acid, adipic acid, pimelic acid, suberic acid, azelaic acid, sebacic acid, chloromalonic acid, dichloromalonic acid, bromomalonic acid, dibromomalonic acid, chlorosuccnic acid, dichlorosuccnic acid, bromosuccnic acid, dibromosuccnic acid, methylsuccnic acid, methylenemalonic acid, α-methylglutaric acid, β-methylglutaric acid, maleic acid, fumaric acid, itaconic acid, citraconic acid, mesaconic acid, glutaconic acid, trans-transmuconic acid, cis-cismuconic acid, cis-transmuconic acid, acetylenedicarboxylic acid, 1-propylene-1,3-dicarboxylic acid, 1-butyne-1,4-dicarboxylic acid, 2-butyne-1,4-dicarboxylic acid, propane-1,2,3-tricarboxylic acid and butane-1,2,3,4-tetracarboxylic acid; and aromatic carboxylic acids such as benzoic acid, o-hydroxybenzoic acid, m-hydroxybenzoic acid, p-hydroxybenzoic acid, 4-acetylbenzoic acid, o-fluorobenzoic acid, phthalic acid, 1,2,4,5-benzenetetracarboxylic acid, 1-naphthoic acid, 2-naphthoic acid, 3-hydroxy-2-naphthoic acid, 4-biphenylcarboxylic acid, 4,4'-biphenyldicarboxylic acid, 9-anthracenedicarboxylic acid, 2-quinolinecarboxylic acid and 4-pyridinecarboxylic acid.

As specific examples of the Lewis acid compounds used as a catalyst in the present invention, there can be mentioned boron trifluoride, boron trichloride, boron tribromide, aluminum chloride, aluminum bromide, iron(III) chloride, iron (III) bromide, antimony trichloride, antimony pentachloride, titanium trichloride, titanium tetrachloride, zinc chloride, zinc bromide, tin chloride, copper chloride, tungsten chloride, iron powder and zeolites.

Among the above-recited catalysts, sulfonic acid compounds such as sulfuric acid and p-toluenesulfonic acid are preferable. Sulfuric acid is especially preferable in view of safety and cost.

The catalysts may be used either alone or as a mixture of at least two thereof.

The amount of the catalyst is not particularly limited, but is usually in the range of $10^{-4}$ mol to 1 mol per mol of the acrylic acid compound of formula (1).

In a preferable example of the process of the present invention, an acrylate compound represented by the following formula (41):

(41)

wherein $R^6$ is a hydrogen atom, a methyl group or a trifluoromethyl group, and $R^{23}$ is 2-methyl-2-adamanthyl group or a 1-methylcyclohexyl group, is produced by allowing an acrylic acid compound represented by the following formula (38):

(38)

wherein $R^6$ is the same as defined above for formula (41), to react with 2-methyleneadamantane or 1-ethylcyclohexene, represented by the following formula (37) or (36), respectively:

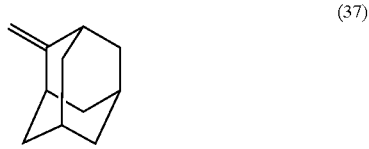

(37)

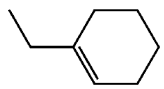
(36)

in the presence of an acid catalyst comprised of sulfuric acid or p-toluenesulfonic acid.

The reaction temperature is not particularly limited, but is usually in the range of –50° C. to 100° C.

The process of the present invention can be carried out in the presence of a solvent. The solvent used is not particularly limited, and, as specific examples thereof, there can be mentioned aliphatic hydrocarbons such as hexane and heptane; aromatic hydrocarbons such as benzene, toluene and xylene; halogenated hydrocarbons such as dichloromethane and dichloroethane; and ethers such as diethyl ether and tetrahydrofuran.

After completion of the reaction, the residual raw materials and catalyst are removed, for example, by washing a reaction mixture with water, and the object acrylate compound can be obtained by conventional purification procedures such as distillation, recrystallization and column chromatography.

The invention will now be specifically described by the following examples that by no means limit the scope of the invention.

REFERENCE EXAMPLE 1

Synthesis of 2-methyleneadamantane

One liter flask equipped with a Dean-Stark condenser was charged with 166.3 g (1.0 mol) of 2-methyl-2-adamantanol (supplied by Sigma-Aldrich Co.), 2.0 g (20 mmol) of sulfuric acid and 500 g of toluene. The content was heated to the solvent reflux temperature. While toluene and water produced through the reaction were collected as an azeotrope by the Dean-Stark condenser, the reaction mixture was refluxed for 2 hours. After completion of the reaction, the catalyst was removed by washing the reaction mixture with water and the obtained organic phase was concentrated to dryness to give 152.5 g of white solid 2-methyleneadamantane (purity: 99.0%, yield: 98.0%).

EXAMPLE 1

Synthesis of 2-methyl-2-adamantyl α-trifluoromethylacrylate [MAFAC]

A 500 ml flask was flushed with nitrogen to displace the air with nitrogen, and was charged with 70.0 g (0.50 mol) of α-trifluoromethylacrylic acid (supplied from Tosoh F-tech Inc.), 1.0 g (10 mmol) of sulfuric acid and 100 g of toluene. Separately 88.8 g (0.60 mol) of 2-methyleneadamantane, prepared by the same procedures as described in Reference Example 1, was dissolved in 100 g of toluene. The obtained solution of 2-methyleneadamantane in toluene was dropwise added to the content in the flask over a period of about 3 hours, while the content was maintained at a reaction temperature of about 5° C. Then the content was stirred for 15 hours at the same temperature. After completion of the reaction, the residual catalyst was neutralized by adding 40.0 g (50 mmol) of a 5% aqueous sodium hydroxide solution, and the neutralized liquid was washed with an aqueous saturated sodium chloride solution. The thus-obtained organic phase was subjected to column chromatography, and further, analyzed by NMR and mass spectrometry. Thus, 133.9 g (yield: 93.0%) of the object 2-methyl-2-adamantyl α-trifluoromethylacrylate was obtained.

Results of Analysis:
(1) $^1$H-NMR (CDCl$_3$):
δ(ppm)=6.73(1H,S), 6.42(1H,S), 1.63–2.43(15H,m)
(2) MS spectrum (m/z): 288(M+)

EXAMPLE 2

Synthesis of 2-methyl-2-adamantyl Acrylate [MAAC]

A 500 ml flask was flushed with nitrogen to displace the air with nitrogen, and was charged with 36.0 g (0.50 mol) of acrylic acid, 0.5 g (5 mmol) of sulfuric acid and 100 g of toluene. Separately 88.8 g (0.60 mol) of 2-methyleneadamantane, prepared by the same procedures as described in Reference Example 1, was dissolved in 100 g of toluene. The obtained solution of 2-methyleneadamantane in toluene was dropwise added to the content in the flask over a period of about 3 hours, while the content was maintained at a reaction temperature of about 20° C. Then the content was stirred for 5 hours at the same temperature. After completion of the reaction, the residual catalyst was neutralized by adding 40.0 g (50 mmol) of a 5% aqueous sodium hydroxide solution, and the neutralized liquid was washed with an aqueous saturated sodium chloride solution. The thus-obtained organic phase was subjected to column chromatography, and further, analyzed by NMR and mass spectrometry. Thus, 100.7 g (yield: 91.5%) of the object 2-methyl-2-adamantyl acrylate was obtained.

EXAMPLE 3

Synthesis of 2-methyl-2-adamantyl Methacrylate [MAMC]

A 500 ml flask was flushed with nitrogen to displace the air with nitrogen, and was charged with 43.0 g (0.50 mol) of methacrylic acid, 0.95 g (5 mmol) of p-toluenesulfonic acid monohydrate (supplied by Wako Pure Chem. Ind. Ltd.) and 100 g of toluene. Separately 74.0 g (0.50 mol) of 2-methyleneadamantane, prepared by the same procedures as described in Reference Example 1, was dissolved in 100 g of toluene. The obtained solution of 2-methyleneadamantane in toluene was dropwise added to the content in the flask over a period of about 3 hours, while the content was maintained at a reaction temperature of about 5° C. Then the content was stirred for 5 hours at the same temperature. After completion of the reaction, the residual catalyst was neutralized by adding 40.0 g (50 mmol) of a 5% aqueous sodium hydroxide solution, and the neutralized liquid was washed with an aqueous saturated sodium chloride solution. The thus-obtained organic phase was subjected to column chromatography, and further, analyzed by NMR and mass spectrometry. Thus, 106.2 g (yield: 90.8%) of the object 2-methyl-2-adamantyl methacrylate was obtained.

REFERENCE EXAMPLE 2

Synthesis of 1-ethylcyclohexanol

One liter flask was flushed with nitrogen to displace the air with nitrogen, and was charged with 26.7 g (1.1 mol) of metallic magnesium (supplied by Aldrich Co.) and 500 g of tetrahydrofuran. Among 109.0 g (1.0 mol) of ethyl bromide (supplied by Kanto Chem. Co.), about 5 g thereof was added to the content in the flask to confirm heat generation due to initiation of the exothermic Grignard reaction, and then the remainder of ethyl bromide was dropwise added over a period of about 1 hour while the inner temperature was controlled so as not to exceed 50° C. Further, the reaction mixture was stirred at the same temperature for 1 hour. Then, 98.2 g (1.0 mol) of cyclohexanone was dropwise added over a period of about 3 hours while the reaction temperature was controlled so as not to exceed 20° C. Further, the reaction mixture was stirred at the same temperature for 1 hour. After completion of the reaction, the reaction mixture was treated with 550 g (1.5 mol) of an aqueous HCl solution and the obtained organic phase was concentrated to dryness to give 127.6 g of a white solid. NMR and mass spectroscopy of the white solid revealed that it was 1-ethylcyclohexanol (purity: 98.5%, yield: 98.0%).

REFERENCE EXAMPLE 3

Synthesis of 1-ethylcyclohexene

One liter flask equipped with a Dean-Stark condenser was charged with 64.1 g (0.5 mol) of 1-ethylcyclohexanol, prepared in Reference Example 2, 1.0 g (10 mmol) of sulfuric acid and 300 g of toluene. The content was heated to the solvent reflux temperature. While toluene and water produced through the reaction were collected as an azeotrope by the Dean-Stark condenser, the reaction mixture was refluxed for 1 hours. After completion of the reaction, the catalyst was removed by washing the reaction mixture with water and the obtained organic phase was distilled under reduced pressure to obtain 58.3 g of colorless liquid as a fraction of 77° C./15 kPa. NMR and mass spectroscopy of the colorless liquid revealed that it was 1-ethylcyclohexene (purity: 96.0%, yield: 87.5%).

EXAMPLE 4

Synthesis of 1-ethylcyclohexyl Methacrylate

A 500 ml flask was flushed with nitrogen to displace the air with nitrogen, and was charged with 43.0 g (0.5 mol) of methacrylic acid, 0.5 g (5 mmol) of sulfuric acid and 100 g of toluene. Separately 110.2 g (1.0 mol) of 1-ethylcyclohexene, prepared by the same procedures as described in Reference Example 3, was dissolved in 100 g of toluene. The obtained solution of 1-ethylcyclohexene in toluene was dropwise added to the content in the flask over a period of about 3 hours, while the content was maintained at a reaction temperature of about 30° C. Then the content was stirred for 15 hours at the same temperature. After completion of the reaction, the residual catalyst was neutralized by adding 40.0 g (50 mmol) of a 5% aqueous sodium hydroxide solution, and the neutralized liquid was washed with an aqueous saturated sodium chloride solution. The thus-obtained organic phase was subjected to column chromatography, and further, analyzed by NMR and mass spectrometry. Thus, 68.6 g (yield: 69.9%) of the object 1-ethylcyclohexyl methacrylate was obtained.

Results of Analysis:

(1) $^1$H-NMR (CDCl$_3$):

$\delta$(ppm)=6.12(1H,S), 5.55(1H,S), 1.25–2.37(15H,m), 0.89 (3H,t)

(2) MS spectrum (m/z): 196(M+)

COMPARATIVE EXAMPLE 1

Synthesis of 2-methyl-2-adamantyl α-trifluoromethylacrylate [MAFAC] from 2-methyl-2-adamantanol and α-trifluoromethylacryloyl chloride A 500 ml flask was flushed with nitrogen to displace the air with nitrogen, and was charged with 83.1 g (0.50 mol) of 2-methyl-2-adamantanol, 101.2 g (1.0 mol) of triethylamine and 200 g of tetrahydrofuran. Then 118.9 g (0.75 mol) of α-trifluoromethylacryloyl chloride was dropwise added to the content in the flask over a period of about 1 hour, while the content was maintained at a reaction temperature of about 0° C. Then the content was stirred for 10 hours at room temperature. After completion of the reaction, the reaction mixture was washed with water and then with an aqueous saturated sodium chloride solution. The thus-obtained organic phase was subjected to column chromatography, and further, analyzed by NMR and mass spectrometry. Thus, 101.2 g (yield: 70.3%) of the object 2-methyl-2-adamantyl α-trifluoromethylacrylate was obtained.

What is claimed is:

1. A process for preparing an acrylate compound represented by the following formula (4-1):

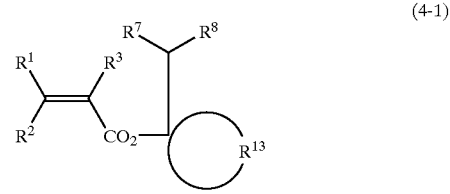

(4-1)

wherein $R^1$ and $R^2$ independently represent a hydrogen atom or a fluorine atom, $R^3$ represents a hydrogen atom, a fluorine atom, an alkyl group, an alkenyl group, a fluoroalkyl group or a fluoroalkenyl group, $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{13}$ represents a $C_2$–$C_{15}$ straight-chain or branched alkylene group or a $C_2$–$C_{15}$ straight-chain or branched alkenylene group, and $R^{13}$ may form an oxygen-containing heterocyclic structure together with the carbon atom to which $R^{13}$ is bonded;

which comprises allowing an acrylic acid compound represented by the following formula (1):

(1)

wherein $R^1$, $R^2$ and $R^3$ are the same as defined above for formula (4-1), to react with an unsaturated compound represented by the following formula (9):

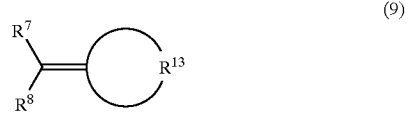

(9)

wherein $R^7$, $R^8$ and $R^{13}$ are the same as defined above for formula (4-1);

wherein said unsaturated compound of formula (9) is selected from the group consisting of:

a compound represented by the following formula (14):

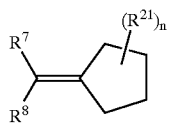
(14)

wherein $R^7$ and $R^8$ are the same as defined above for formula (4-1), and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 8;

a compound represented by the following formula (15):

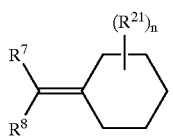
(15)

wherein $R^7$, $R^8$ and $R^{21}$ are the same as defined above for formula (14), and n is an integer in the range of 0 to 10;

a compound represented by the following formula (16):

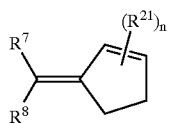
(16)

wherein $R^7$, $R^8$ and $R^{21}$ are the same as defined above for formula (14), and n is an integer in the range of 0 to 6;

a compound represented by the following formula (17):

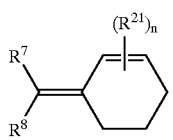
(17)

wherein $R^7$, $R^8$ and $R^{21}$ are the same as defined above for formula (14), and n is an integer in the range of 0 to 8;

a compound represented by the following formula (18):

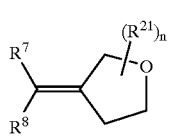
(18)

wherein $R^7$, $R^8$ and $R^{21}$ are the same as defined above for formula (14), and n is an integer in the range of 0 to 6;

a compound represented by the following formula (19):

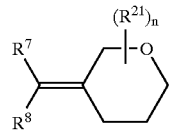
(19)

wherein $R^7$, $R^8$ and $R^{21}$ are the same as defined above for formula (14), and n is an integer in the range of 0 to 8; and a compound represented by the following formula (20):

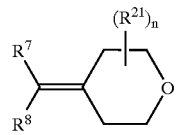
(20)

wherein $R^7$, $R^8$ and $R^{21}$ are the same as defined above for formula (14), and n is an integer in the range of 0 to 8.

2. The process according to claim 1, wherein the acrylic acid compound is represented by the following formula (5):

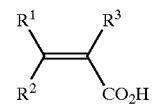
(5)

wherein $R^1$ and $R^2$ independently represent a hydrogen atom or a fluorine atom, and $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

3. The process according to claim 1, wherein the acrylic acid compound is represented by the following formula (6):

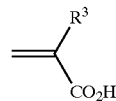
(6)

wherein $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

4. The process according to claim 1, wherein the acrylic acid compound is selected from the group consisting of α-trifluoromethylacrylic acid, α-trifluoroethylacrylic acid, α-perfluoroethylacrylic acid, α-perfluoropropylacrylic acid, α-perfluorobutylacrylic acid, α-fluoroacrylic acid, acrylic acid and methacrylic acid.

5. The process according to claim 1, wherein the acrylic acid compound is selected from the group consisting of α-trifluoromethylacrylic acid, acrylic acid and methacrylic acid.

6. A process for preparing an acrylate compound represented by the following formula (4-2):

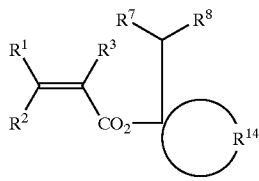
(4-2)

wherein $R^1$ and $R^2$ independently represent a hydrogen atom or a fluorine atom, $R^3$ represents a hydrogen atom, a fluorine atom, an alkyl group, an alkenyl group, a fluoroalkyl group or a fluoroalkenyl group, $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, and $R^{14}$ represents a $C_1$–$C_{15}$ alkylene group, or a $C_2$–$C_{15}$ alkenylene group, and $R^{14}$ may form an oxygen-containing heterocyclic structure together with the carbon atom to which $R^{14}$ is bonded;

which comprises allowing an acrylic acid compound represented by the following formula (1):

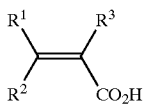
(1)

wherein $R^1$, $R^2$ and $R^3$ are the same as defined above for formula (4-2), to react with an unsaturated compound represented by the following formula (10):

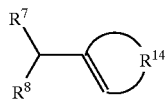
(10)

wherein $R^7$, $R^8$ and $R^{14}$ are the same as defined above for formula (4-2);

wherein said unsaturated compound of formula (10) is selected from the group consisting of:

a compound represented by the following formula (21):

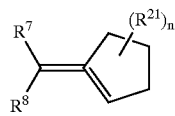
(21)

wherein $R^7$ and $R^8$ are the same as defined above for formula (4-2), and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 7;

a compound represented by the following formula (22):

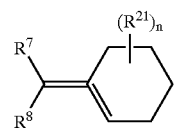
(22)

wherein $R^7$, $R^8$ and $R^{21}$ are the same as defined above for formula (21), and n is an integer in the range of 0 to 9;

a compound represented by the following formula (23):

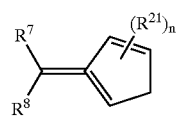
(23)

wherein $R^7$, $R^8$ and $R^{21}$ are the same as defined above for formula (21), and n is an integer in the range of 0 to 5;

a compound represented by the following formula (24):

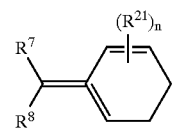
(24)

wherein $R^7$, $R^8$ and $R^{21}$ are the same as defined above for formula (21), and n is an integer in the range of 0 to 7;

a compound represented by the following formula (25):

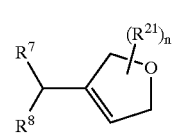
(25)

wherein $R^7$, $R^8$ and $R^{21}$ are the same as defined above for formula (21), and n is an integer in the range of 0 to 5;

a compound represented by the following formula (26):

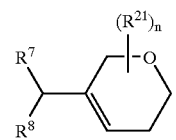
(26)

wherein $R^7$, $R^8$ and $R^{21}$ are the same as defined above for formula (21), and n is an integer in the range of 0 to 7; and a compound represented by the following formula (27):

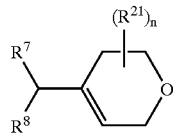

(27)

wherein $R^7$, $R^8$ and $R^{21}$ are the same as defined above for formula (21), and n is an integer in the range of 0 to 7.

7. The process according to claim 6, wherein the acrylic acid compound is represented by the following formula (5):

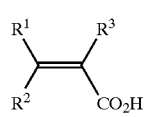

(5)

wherein $R^1$ and $R^2$ independently represent a hydrogen atom or a fluorine atom, and $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

8. The process according to claim 6, wherein the acrylic acid compound is represented by the following formula (6):

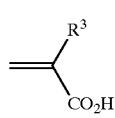

(6)

wherein $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

9. The process according to claim 6, wherein the acrylic acid compound is selected from the group consisting of α-trifluoromethylacrylic acid, α-trifluoroethylacrylic acid, α-perfluoroethylacrylic acid, α-perfluoropropylacrylic acid, α-perfluorobutylacrylic acid, α-fluoroacrylic acid, acrylic acid and methacrylic acid.

10. The process according to claim 7, wherein the acrylic acid compound is selected from the group consisting of α-trifluoromethylacrylic acid, acrylic acid and methacrylic acid.

11. A process for preparing an acrylate compound represented by the following formula (4-3):

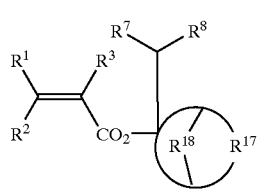

(4-3)

wherein $R^1$ and $R^2$ independently represent a hydrogen atom or a fluorine atom, $R^3$ represents a hydrogen atom, a fluorine atom, an alkyl group, an alkenyl group, a fluoroalkyl group or a fluoroalkenyl group, $R^7$ and $R^8$ independently represent a hydrogen atom, a halogen atom, a $C_1$–$C_4$ straight-chain or branched alkyl group, a $C_2$–$C_4$ straight-chain or branched alkenyl group, a $C_1$–$C_4$ straight-chain or branched haloalkyl group, or a $C_2$–$C_4$ straight-chain or branched haloalkenyl group, $R^{17}$ represents a $C_1$–$C_{15}$ alkylene group or a $C_2$–$C_{15}$ alkenylene group, and $R^{18}$ represents a $C_1$–$C_3$ alkylene group;

which comprises allowing an acrylic acid compound represented by the following formula (1):

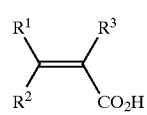

(1)

wherein $R^1$, $R^2$ and $R^3$ are the same as defined above for formula (4), to react with an unsaturated compound represented by the following formula (12):

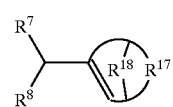

(12)

wherein $R^7$, $R^8$, $R^{17}$ and $R^{18}$ are the same as defined above for formula (4-3);

wherein said unsaturated compound of formula (12) is selected from the group consisting of:

a compound represented by the following formula (32):

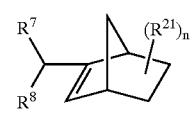

(32)

wherein $R^7$ and $R^8$ are the same as defined above for formula (4-3), and $R^{21}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_1$–$C_4$ alkoxy group, an amino group, a carboxyl group, an ester group, a carbonyl group or a halogen atom, and n is an integer in the range of 0 to 8;

a compound represented by the following formula (33):

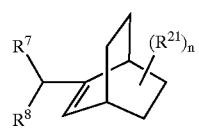

(33)

wherein $R^7$, $R^8$ and $R^{21}$ are the same as defined above for formula (32), and n is an integer in the range of 0 to 8;

a compound represented by the following formula (34):

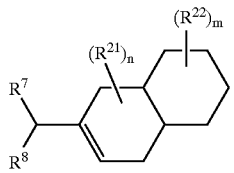

(34)

wherein $R^7$, $R^8$ and $R^{21}$ are the same as defined above for formula (32), n is an integer in the range of 0 to 5, $R^{22}$ independently represents a $C_1$–$C_4$ straight-chain or branched alkyl group, a $C_2$–$C_4$ straight-chain or branched alkenyl group, a $C_1$–$C_4$ straight-chain or branched haloalkyl group, a $C_2$–$C_4$ straight-chain or branched haloalkenyl group, a hydroxyl group, a $C_2$–$C_4$ alkoxy group, an amino group, a carboxyl group, an ester group, a carbonyl group or a halogen atom, and m is an integer in the range of 0 to 8; and a compound represented by the following formula (35):

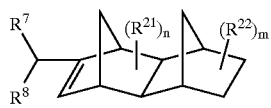

(35)

wherein $R^7$, $R^8$, $R^{21}$ and $R^{22}$ are the same as defined above for formulae (32) and (34), and n is an integer in the range of 0 to 8, and m is an integer in the range of 0 to 8.

12. The process according to claim 11, wherein the acrylic acid compound is represented by the following formula (5):

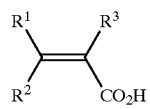

(5)

wherein $R^1$ and $R^2$ independently represent a hydrogen atom or a fluorine atom, and $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

13. The process according to claim 11, wherein the acrylic acid compound is represented by the following formula (6):

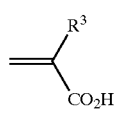

(6)

wherein $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

14. The process according to claim 11, wherein the acrylic acid compound is selected from the group consisting of α-trifluoromethylacrylic acid, α-trifluoroethylacrylic acid, α-perfluoroethylacrylic acid, α-perfluoropropylacrylic acid, α-perfluorobutylacrylic acid, α-fluoroacrylic acid, acrylic acid and methacrylic acid.

15. The process according to claim 11, wherein the acrylic acid compound is selected from the group consisting of α-trifluoromethylacrylic acid, acrylic acid and methacrylic acid.

16. A process for preparing an acrylate compound represented by the following formula(4-4):

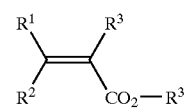

(4-4)

wherein $R^1$ and $R^2$ independently represent a hydrogen atom or a fluorine atom, $R^3$ represents a hydrogen atom, a fluorine atom, an alkyl group, an alkenyl group, a fluoroalkyl group or a fluoroalkenyl group, and $R^{23}$ is a 1-ethylcylohexyl group represented by the following formula (43):

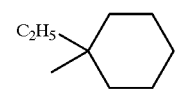

(43)

or a 2-methyl-2-adamantyl group represented by the following formula (44):

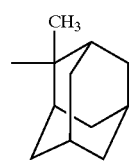

(44)

which comprises allowing an acrylic acid compound represented by the following formula (1):

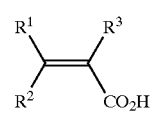

(1)

wherein $R^1$, $R^2$ and $R^3$ are the same as defined above for formulae (4-4) and (4-5), to react with 1-ethylcyclohexene represented by the following formula (36):

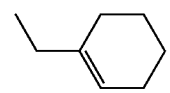

(36)

or 2-methyleneadamantane represented by the following formula (37):

(37)

17. The process according to claim 16, wherein the acrylic acid compound is represented by the following formula (5):

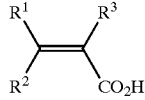
(5)

wherein $R^1$ and $R^2$ independently represent a hydrogen atom or a fluorine atom, and $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

18. The process according to claim 16, wherein the acrylic acid compound is represented by the following formula (6):

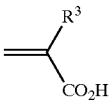
(6)

wherein $R^3$ represents a hydrogen atom, a fluorine atom, a $C_1$–$C_4$ straight-chain or branched alkyl group, a $C_2$–$C_4$ straight-chain or branched alkenyl group, a $C_1$–$C_4$ straight-chain or branched fluoroalkyl group, or a $C_2$–$C_4$ straight-chain or branched fluoroalkenyl group.

19. The process according to claim 16, wherein the acrylic acid compound is selected from the group consisting of α-trifluoromethylacrylic acid, α-trifluoroethylacrylic acid, α-perfluoroethylacrylic acid, α-perfluoropropylacrylic acid, α-perfluorobutylacrylic acid, α-fluoroacrylic acid, acrylic acid and methacrylic acid.

20. The process according to claim 16, wherein the acrylic acid compound is selected from the group consisting of α-trifluoromethylacrylic acid, acrylic acid and methacrylic acid.

* * * * *